United States Patent
Robb et al.

(10) Patent No.: US 8,030,006 B2
(45) Date of Patent: *Oct. 4, 2011

(54) BLOOD TYPING

(75) Inventors: Janine Robb, Midlothian (GB); Linda K. Knowles, Midlothian (GB); Juraj Petrik, Peebles (GB)

(73) Assignee: Alba Bioscience Limited, Edinburgh (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/441,784

(22) PCT Filed: Sep. 16, 2007

(86) PCT No.: PCT/GB2007/003514
§ 371 (c)(1),
(2), (4) Date: Sep. 17, 2009

(87) PCT Pub. No.: WO2008/035047
PCT Pub. Date: Mar. 27, 2008

(65) Prior Publication Data
US 2010/0041565 A1    Feb. 18, 2010

(30) Foreign Application Priority Data
Sep. 20, 2006 (GB) .................................. 0618496.4

(51) Int. Cl.
*G01N 33/53* (2006.01)

(52) U.S. Cl. ........................... 435/7.1; 435/7.2; 436/518

(58) Field of Classification Search ........................ None
See application file for complete search history.

(56) References Cited

U.S. PATENT DOCUMENTS 6,822,078 B2 * 11/2004 Ozaki et al. .................. 530/358
2007/0003979 A1 * 1/2007 Worthington .................. 435/7.1

FOREIGN PATENT DOCUMENTS

| CA | 2365178 A1 | | 6/2003 |
| EP | 0223978 | * | 3/1986 |
| WO | WO 2006/100477 A1 | | 9/2006 |

OTHER PUBLICATIONS

Campbell et al. "Cell Interaction Microarray for Blood Phenotyping" *Anal. Chem.* 78:1930-1938 (2006).
Robb et al. "Development of non-agglutination microarray blood grouping", *Transfusion Medicine* 16:119-129 (2006).
Notification of Transmittal of the International Search Report and the Written Opinion of the International Searching Authority, or the Declaration corresponding to International Patent Application No. PCT/GB2007/003514 mailed Jan. 2, 2008.

* cited by examiner

*Primary Examiner* — Jacob Cheu
(74) *Attorney, Agent, or Firm* — Myers Bigel Sibley & Sajovec, P.A.

(57) ABSTRACT

A blood testing method for use in the detection of a disease, wherein at least one characteristic antibody or complement factor is bound to a subject's red blood cells, comprises providing a microarray wherein a plurality of binding agents therefor are immobilized on a substrate at discrete pre-defined positions; and contacting a blood sample therewith. The presence of bound red blood cells is then detected.

20 Claims, 3 Drawing Sheets

BLOOD TYPING

CROSS-REFERENCE TO RELATED APPLICATIONS

This application is a 35 U.S.C. §371 national phase application of PCT Application No. PCT/GB2007/003514, filed on Sep. 16, 2007, which claims priority from Great Britain Patent Application No. 0618496.4, filed on Sep. 20, 2006, the disclosures and contents of which are incorporated by reference herein in their entireties. The above-referenced PCT International Application was published in the English language as International Publication No. WO 2008/035047 A1.

FIELD OF THE INVENTION

The present invention relates to blood typing, and more particularly to the detection of particular phenotypes, characterized by particular antibodies present on the surface of erythrocytes.

BACKGROUND OF THE INVENTION

The direct Coombs test (also known as the direct antiglobulin test or DAT or DAGT) is used to detect if antibodies or complement system factors have been bound to erythrocyte or red blood cells (RBC) surface antigens in vivo. Such bound antibodies are associated with various diseases in which an immune mechanism is attacking the patient's own RBCs. This mechanism could be autoimmunity alloimmunity or a drug-induced immune-mediated mechanism. In more detail such diseases include:
Examples of Alloimmune Haemolysis
Hemolytic disease of the newborn (also known as HDN or erythroblastosis fetalis)
Rhesus D hemolytic disease of the newborn (also known as Rh disease)
ABO hemolytic disease of the newborn (the indirect Coombs test may only be weakly positive)
Anti-Kell hemolytic disease of the newborn
Rhesus c hemolytic disease of the newborn
Other blood group incompatibility (RhC, Rhe, RhE, Kid, Duffy, MN, P and others)
Alloimmune haemolytic transfusion reactions
Examples of Autoimmune Haemolysis
Warm antibody autoimmune hemolytic anemia
Idiopathic
Systemic lupus erythematosus
Evans' syndrome (antiplatelet antibodies and haemolytic antibodies)
Cold antibody autoimmune hemolytic anemia
Idiopathic cold hemagglutinin syndrome
Infectious mononucleosis
Paroxysmal cold hemoglobinuria (rare)
Drug-induced immune-mediated haemolysis
Methyldopa
Penicillin (high dose)

The complement system is composed of a number of small proteins found in the blood, which co-operate with the antigen-antibody interaction to kill target cells. Over 20 proteins and protein fragments make up the complement system.

Conventionally the DAT test has been carried out as an agglutination test in a test tube. More recently this test has also been carried out using agglutination microplate and gel technology. The test however, is still somewhat cumbersome and automated read-out of the results can be problematic.

More recently it has been found that ABO blood typing can be successfully carried out using non-agglutination protein microarrays, in which an immobilized antibody binds to an antigen on the surface of the RBC, and the presence of RBCs so immobilized is detected (J S Robb et al 2006). It has further been found that antibody microarray technology can be used to phenotype erythrocytes by detecting complex mixtures of antigens on cell surfaces (C J Campbell et al 2006). The antigens are both sugar antigens, which tend to be well presented and easily accessible, and peptide antigens, which are epitopes of transmembrane proteins and therefore buried and held more closely to the cell surface, and these were successfully differentiated using the correct choice of antibodies.

We have now surprisingly found that RBCs coated with antibody and/or complement (protein) can withstand the required processing and remain 'sensitised' (coated) with said antibody or complement bound to said RBCs, and that microarray technology can be used to detect antibodies and/or complement present on the surface of RBCs, thereby providing a test which is a much more efficient and an effective alternative to conventional DAT testing, and which can, moreover, be readily integrated into a single microarray with other tests important in blood processing—including blood grouping phenotyping for multiple antigens on the surface of the RBC.

SUMMARY OF THE INVENTION

Thus in a first aspect the present invention provides, a blood testing method suitable for use in the detection of a disease in which an immune mechanism may be attacking the subject's own RBCs and is characterized by at least one characteristic antibody/complement factor bound to said RBCs, which method comprises the steps of:
providing a microarray having immobilized on a substrate at discrete pre-defined positions, a plurality of binding agents which are capable of binding specifically to different said characteristic antibodies/complement factor; contacting a blood sample from the subject with said microarray;
substantially removing any unbound RBCs from at least an area of said substrate to which said binding agents are bound; and
detecting the presence of RBCs bound (through said characteristic antibodies) to said microarray, in order to determine the presence of any said characteristic antibody/complement factor bound to the subject's RBCs.

Whilst the use of protein microarrays for binding antibodies has been previously known, it is very surprising that the RBCs bound by the characteristic antibodies, can survive the further processing required for detection of said RBCs and remain attached thereto and thereby captively held to the microarray. Further processing involves washing of the microarray to remove unbound matter and reduce non-specific binding, plus drying to allow scanning to be performed.

In another aspect the present invention provides a protein microarray for use in the detection of a disease in which an immune mechanism is attacking the subject's own RBCs and is characterized by at least one characteristic antibody or complement factor bound to said RBCs, which protein microarray has immobilized on a substrate at discrete pre-defined positions, a plurality of binding agents which are capable of binding specifically to different said characteristic antibodies/complement factor.

DETAILED DESCRIPTION OF THE INVENTION

Figure 1:
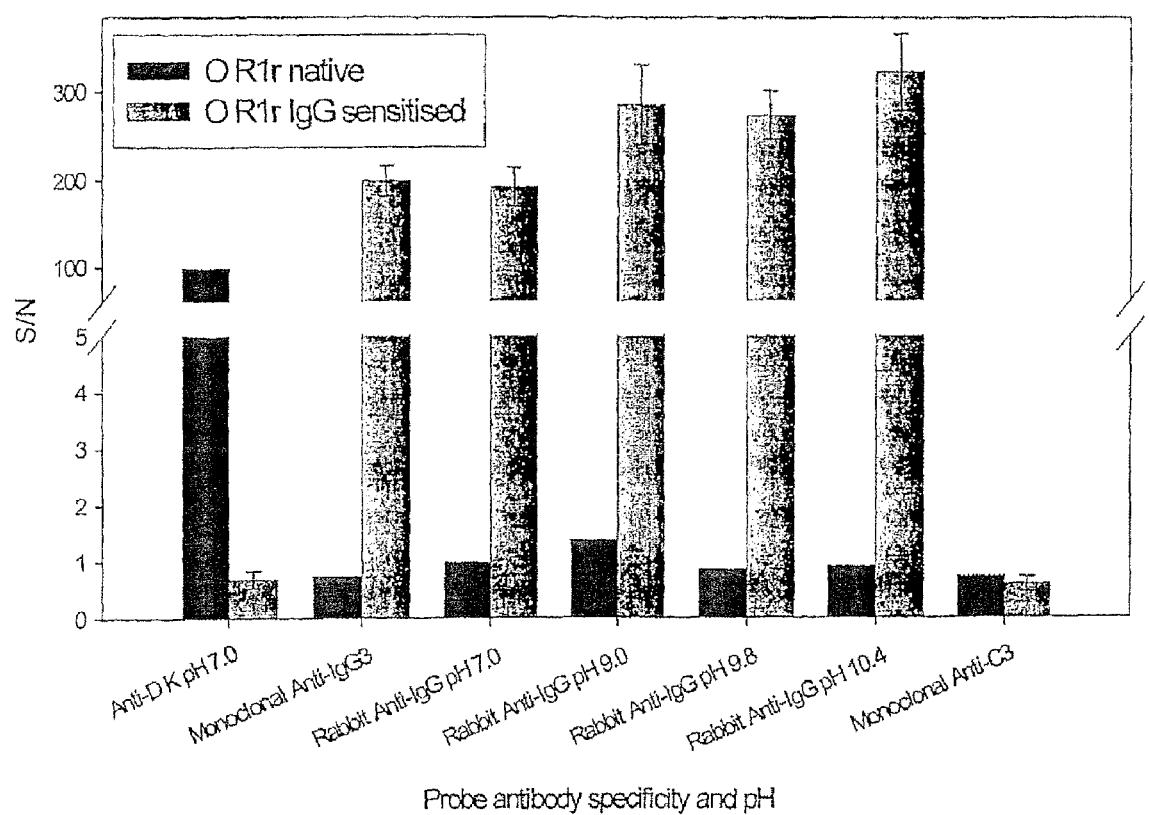
FIG. 1 depicts the results of the DAT testing of blood using protein microarrays as described in Example 4 and analyzed in Example 5.

The novel form of DAGT testing of the present invention with multiple discrete probes on a single test system and at the same time, which facilitates combining blood grouping, phenotyping and DAGT, will improve the efficiency and effectiveness of blood test procedures by allowing the identification and differentiation of different DAGT coatings of different characteristic antibodies and/or complement factor. This will also minimize delays in determining the clinical significance of the DAGT coating.

In general suitable binding agents comprise antibodies or antibody fragments specific for the characteristic antibody or complement factor to be detected. However, other specifically reactive binding agents, such as small molecule antibody mimetics, nucleic acid ligands, or receptors from other cells which are capable of binding said antigens may be employed. Lectins may also be employed. However, for simplicity reference hereinafter will be made to antibodies, but this should not be construed as limiting.

It will be appreciated that the choice of binding agents provided on the microarray will depend on the identity of the target characteristic antibodies. In general the binding agents would correspond to those used in conventional DAT testing i.e. at least anti-$IgG_1$, anti-$IgG_3$, and anti-complement (C3). Preferably they would also include a broad spectrum anti-IgG). Advantageously they would also include anti-$IgG_2$ and $IgG_4$. If desired other antibodies could also be included such as for example, anti-light chain λ, or anti-light chain κ.

The binding agent antibodies immobilized on the substrate may be polyclonal or monoclonal.

Polyclonal antibodies are heterogeneous populations of antibody molecules derived from the sera of animals immunized with an antigen, or an antigenic functional derivative thereof. For the production of polyclonal antibodies, host animals for example rabbits, sheep, pigs, etc., can be immunized by injection with a specific antigen optionally supplemented with adjuvants.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. U.S.A. 80:2026-2030), and the EBV-hybridoma technique (Cole et al., 1985, Monoclonal Anti-bodies and Cancer Therapy, Alan R. Liss, Inc., pp. 77-96).

Such antibodies can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

In addition, techniques for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454; U.S. Pat. No. 4,816,567) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778: Bird, 1988, Science 242:423-426; Huston et al., 1988, Proc. Natl. Acad. Sci. U.S.A. 85:5879-5883; and Ward et al., 1989, Nature 334:544-546) and for making humanized monoclonal antibodies (U.S. Pat. No. 5,225,539) can be utilized. Antibody fragments which recognize specific epitopes can be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries can be constructed (Huse et al., 1989, Science, 246:1275-1281) to allow rapid and easy identification of monoclonal Fab fragments with the desired specificity.

In the case of the present invention there would conveniently be used a monoclonal anti-$IgG_1$, a monoclonal anti-$IgG_3$, and a monoclonal anti-C3. When anti-IgG is included, this is conveniently a (polyclonal) anti-IgG.

The antibodies are bound to the substrate in an array. As used herein the term "array" refers to a generally ordered arrangement of bound antibodies, that specifically bind to red blood cell antigens, especially cell surface antigens, on a substrate such as glass. Typically the array may be in the form of a series of regularly spaced apart delimited areas to which the antibodies are bound. Such substrate bound antibody arrays may be commonly described as an "antibody chip".

The antibodies may be arranged on for example, a flat or spherical substrate referred hereto as a "chip" so that there are preferably at least one or more different antibodies, more preferably at least about 2 antibodies, still more preferably at least about 4 antibodies are bound to the surface of the substrate. Moreover, each specific antibody may be provided in a number of dilutions and/or repeated a number of times (e.g. 3-10 times), in order to minimise any false positive or negative reactions which may occur, when carrying out a method of detection.

The array can be made of any conventional substrate, for example glass, silicon, silicon oxide, metals and metal oxides either bare or functionalised with functional polymers such as glycidoxypropyltriethoxysilane, poly-1-lysine, aminopropylsilane, carboyxsilane, hydrogels and polymer-brushes, self-assembled monolayers of e.g. functionalised alkyl thiols.

As discussed hereinafter, a particularly convenient method of detection of the bound RBCs involves the use of fluorescence thereof. In this case it can be advantageous to utilise gold coated substrates. Fluorescence of cells, especially red blood cells can increase on gold coated substrates in comparison to non-gold coated substrates. Without wishing to be bound by theory, this can be explained in terms of the special optical properties that films of gold exhibit. Within 7 nm of the gold surface, non-radiative energy transfer will occur between the excited fluorophore and the surface and this property has been used to good effect in the design of "molecular beacons" (Du et al., J. Am. Chem. Soc., 2003, 125, 4012-4013). This will result in a quenching of the emitted light and a concomitant decrease in the fluorescent signal associated with a spot. Since red blood-cells are roughly 6-8 micron in diameter and 1 micron in depth, 99% of the cell volume is outside this area, meaning that the signal is not quenched. However, when fluorescence of red cells spotted on gold slides is compared with those on epoxy silane slides, the fluorescence of the blood cells on the gold slides is higher. This can be explained in terms of another optical quality of noble metal films, the ability to form an evanescent field at the surface. The evanescent wave is a non-propogating light wave that extends from the surface for hundreds of nanometers. Positioning of a fluorophore in this field will enhance the intensity of light emitted from it. While the power of the evanescent wave will be dependant on the angle at which the laser strikes the gold surface, there is still likely to be some enhancement even when using a non-optimized scanner as has been shown using slides printed with a grating pattern (Neuschafer, D., Budach, W., Wanke, C., Chibout, S.-D., Biosens. Bioelectronics 2003, 18, 489-497). The enhanced fluorescence caused by the excitation of red blood-cells by a surface-confined light wave is what causes the signal from spots of blood on gold to emit a higher intensity of light than on the epoxy-silane coated films. This is a significant advantage of the use of gold as a microarray surface. Again without being bound by theory, the inventors consider that since the difference between fluorescence quenching and evanescent enhancement of signal is caused by a distance dependence, gold is a preferred surface to work with for a range of assays. Gold can be easily functionalised using well established techniques for self assembled monolayer formation (Datwani, S. S., Vijayendran, R. A., Johnson, E., Biondi, S. A., Langmuir 2004, 20, 4970-4976), meaning that the distance between a fluorophore and the gold surface can be tuned by, for example, the length of an alkyl chain (Imahori, H. Norieda, H., Nishimura, Y., Yamazaki, I., Higuchi, J., Kato, N., Motohiro, T., Yamada, H., Tamaki, K., Arimura, M., Sakata, Y., J. Phys, Chem. B. 2000, 104, 1253-1260) and the surface chemistry can be easily controlled by the choice of end group. This approach means that the antibodies used in an assay can be positioned such that red blood cells bind within the evanescent field without being quenched. To take full advantage of this process the surface roughness of the gold may need to be optimised since this will improve the enhancement and the configuration of the microarray scanner would have to be matched to the plasmon resonance angle. The array can be in any shape that can be read, including planar and spheroid. Preferred substrates are any suitable rigid or semi-rigid support including membranes, filter, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the antibodies are bound. Preferred substrate surface architecture for improving fluorescent detection are described in WO02/059583 and WO03/023377. In certain embodiments, the substrates are preferably optically transparent.

Generally speaking the "antibody chips" of the present invention may comprise small planar substrates, such as 50-100 mm, e.g. 76 mmcm×15-50 mm, e.g. 26 mm. c, with spot size between 50 and 1000 μm, and up to 10000 spots of antibodies per slide. Conveniently each antibody may be spotted, printed or otherwise bound to the substrate using known techniques, see for example Michael J. Heller, Annual Review of Biomedical Engineering, 2002 Vol. 4: 129-153. DNA Microarray Technology Devices, Systems and Applications. Angenendt, P.; Glökler, J.; Murpy, D.; Lehrach, H.; Cahill, D. J. Anal. Biochem., 2002, 309, 252-260 Angendt, P.; Glökler, J.; Sobek, J.; Lehrach, H.; Cahill, D. J. Chromatogr. A, 2003 100, 997-104. Typical spots are less than 1 mm in diameter, such as less than 500 m or 100 m in diameter. In this manner 10s to 1000s of antibody spots may be provided in a single array, if so required.

The "antibody chips" of the present invention may also be used to test more than one sample. In this manner, each chip may comprise a plurality of separate arrays on the surface of the substrate, arranged in a manner to allow separate samples to be contacted with each array in such a way such that the samples do not mix. For example, each array may be bounded by a wall, ridge, dam, hydrophobic zone or the like designed to prevent different samples from coming into contact with one another.

Various procedures are well known in the art for immobilizing antibodies on microarray substrates. Conveniently electrostatic binding is used to immobilize the antibodies. Other methods of attachment which could be employed include hydrophobic/hydrophilic interactions, chemical interactions, and amine coupling. Adsorption can be direct onto gold substrate via sulphur containing amino acids (cysteine, methionine) as is preferred herein, or binding can be via alkanethiols previously bound to the gold substrate, and containing various functional groups at the other end to react with proteins.

Desirably any areas of the substrate surface not provided with binding agent which could provide non-specific binding sites are desirably treated with blocking agents in order to prevent any non-specific binding of the RBCs and/or antibodies or complement factor bound to said RBCs Various suitable blocking agents are well known in the art.

In general they comprise an albumin or serum (free of undesirable antibodies such as blood group antibodies, anti-IgG antibodies or those that could interfere with any test probe interactions on the same microarray), such as non-fat milk protein, casein, bovine serum albumin (BSA), etc, conveniently presented in a buffer. One convenient example which may be mentioned is 1% w/v bovine serum albumin (BSA) (ID Bio, France) in Phosphate Buffered Saline (PBS) (0.15 M sodium chloride, 2.632 M Phosphate Buffer Stock Solution (Alba Bioscience, Scotland), pH 7.0).

Any RBCs present in the sample of blood which have a said characteristic antibody/complement factor bound thereto, are allowed to specifically react with said bound antibodies over a period of time, such as 10 seconds to several hours, for example 1 minute to 60 minutes. Typically, this may be carried out at room temperature, but may also be carried out at, for example, 37° C.

Removal of unbound material may be achieved by, for example, washing the surface of the substrate with a solution such as water or saline, by blowing or sucking air across the surface of the substrate, or by using centrifugation, or shaking to dispel unbound material from the surface of the substrate. Moreover, areas of the substrate outwith the delimited areas to which the antibodies are bound, may be porous to cells from the sample being tested, such that cells which do not come into contact with the antibodies pass through the substrate and are thereby easily removed.

The presence of the captively held RBCs may be detected by means of various techniques known in the art such as secondary labeling detection (fluorescent, chemiluminescent conjugated antibodies), rolling circle amplification. Conveniently they may be detected by means of the autofluorescence of the RBCs as described in C J Campbell et al 2006, which has the particular advantage of avoiding the need for the use of any labeling and providing a particularly simple form processing. In more detail the RBCs may be irradiated or excited with light of wavelength about 420 nm, 488 nm, 543 nm or 580 nm, and fluorescent emission detected at a longer wavelength such as 530 nm if excited at 488 nm or 570-585 nm if excited at 543 nm.

Thus, if any RBCs bind to the microarray, this may be detected by a fluorescent signal. By knowing the position of each specific antibody on the substrate, it is possible to identify which antigens are present on the surface of the red blood cells being tested and thus identify the blood group of the sample of blood being tested.

Any fluorescence may be detected by any suitable photodetector known in the art, such as a spectrophotometer. Conveniently there may be used a confocal scanner with the exciting laser, with the fluorescent output being detected by the scanner and the intensity thereof given a numerical value for purposes of interpretation and data processing. By using appropriate electronics and software, any device can be programmed to know the identity and location of specific antibodies on the surface of the substrate and to correlate this with fluorescent signals generated, so that a particular blood grouping can be determined and identified to the tester. Additionally, statistical software may be included so as to combine and formulate the results from the various repetitions and/or dilutions of the antibodies provided on the substrate. In this manner, the fluorescent signals obtained from a multiplicity of specific antibody spots may be factored together and a statistically significant result displayed to the tester.

Further preferred features and advantages of the invention will appear from the following detailed Examples given by way of illustration.

EXAMPLE 1

Purification of IgG$_1$ Antibody Binding Agent

ProSep Guard Column and ProSep A High Capacity (Millipore, U.K.) were washed using PBS pH 7.4, pumped at 60 rpm using a Watson Marlow 505S pump. One mm bore silicon tubing was used, with a flow rate of 20 ml/minute. Material for purification was loaded followed by 400 ml of ProSep wash buffer. Bound antibody was eluted using ProSep elution buffer pH 3.0. The pH of the output was adjusted to pH 9.0 using 1M NaOH before dialysis into PBS pH 7.4.

EXAMPLE 2

Purification of other Binding Agents

ProSep G High Capacity (Millipore, U.K.) was washed in PBS pH 7.4 and used to purify other binding agents indicated below, using essentially the same process as described in Example 1.

| Specificity and identity in results | Cell line/ Identity | Antibody Class | Concentration (mg/ml) |
|---|---|---|---|
| Monoclonal Anti-IgG$_3$ | LG3A | IgG | 1.20 |
| Rabbit Anti-IgG | Rabbit polyclonal | IgG | 0.39 |
| Monoclonal Anti-C$_3$ | 3G8 | IgG | 1.00 |

EXAMPLE 3

Preparation of Protein Microarrays

Gold (BioGold) surface coated slides obtained from Erie Scientific were used as the substrate. The binding agent antibody probe samples to be spotted were prepared in PBS. The slides were printed using a SpotBot (Telechem/Arrayit) or BioRobotics MicroGrid II Arrayer with solid pins between 200 μm and 700 μm. Replicates of each sample were printed on each slide, and the slides were air dried for at least one hour, before being sealed in a bag and placed at 4° C. until required. The slides were rinsed briefly in PBS before being treated in a container of PBS-BSA blocking agent for one hour at room temperature, with constant mixing. On removal the slides were rinsed briefly in PBS and centrifuged to dryness in a centrifuge at 1000 rpm for one minute.

EXAMPLE 4

DAT Testing of Blood Using Protein Microarrays

A chamber was placed over each of the protein microarrays prepared according to Example 3. A blood sample from a subject was washed at least 4 times in PBS. An RBC solution for adding to the microarray was prepared by suspending the blood sample to a 1% haematocrit in PBS-BSA. 450 μl of the RBC solution was then pipetted through one of the portholes in the chamber onto the microarray slides. The portholes were sealed with the provided port seals. The slides were placed in a slide box and mixed for one hour at room temperature.

The RBC blood samples contained group C R1r cells sensitised with anti-D 'K' (LHM169/80). Blood samples with Un-sensitised group O R1r cells (native) were also tested.

The chamber was removed and slides briefly submerged into PBS to remove excess target solution. This was followed by two washes in PBS for 10 minutes. After the final wash the slides were centrifuged to dryness and stored in a dust-free dark place until scanning.

EXAMPLE 5

Data Extraction and Analysis

Slides were scanned in an Genepix Personal 4100A Scanner or similar. Wavelength settings to detect RBC autofluorescence were used as described hereinbefore. All slide scans were performed at 10 micron pixel size and saved as both a BMP and a TIF file.

Numerical data was extracted from the microarrays using GenePix Pro 4.1 (Axon Instruments) or similar. The software controls the scanning, data input and date extraction from the microarray. A text input file was self-generated using microarray column and row positions to determine identity and location of each probe. This was used to generate an array list that was loaded once the microarray grid settings had been set up. Once the grid and the array list had been generated, the data was extracted to a text file. This process gave the median fluorescence intensity value from the centre of each spot and a median background value from the entire background area of the slide. This information was collected into an Excel worksheet.

For each spot the background fluorescence value was subtracted from the fluorescence intensity value. For each slide the signal intensity values from each different scan setting were collated into one worksheet. A scatter plot was prepared using all values for each of the settings set against each other. The shape of the resulting data cloud gave an indication of the scan qualities, and can show if settings were too low, or if settings were too high giving saturated spots. The R2 value was applied to each graph and those that gave a value closest to one demonstrated the best data. One scan from each slide was selected for further data processing.

Once the best data scan had been selected it was processed as follows. Unwanted data were removed from the worksheet to leave only one value per spot on the microarray (the fluorescence intensity value minus the background fluorescence value for each spot). The negative control values were used to calculate a 'noise' value—the mean plus two standard deviations of the negatives (mean+2sd). This value represents non-specific binding (NSB). The value for each spot was divided by the mean+2sd of the negative controls to give a signal-to-noise ratio (S/N). Values over one can be considered significant. The median of the S/N was calculated for the replicate spots of each sample.

Using Microsoft Excel the processed data was analysed as appropriate. Bar charts were used throughout to analyse data. The Y-axis on the bar charts represents the S/N median for the sample.

Where error bars were included, the standard error for each sample was calculated as follows. The standard deviation of the replicates of each sample was calculated (this was performed on S/N ratios or actual fluorescence values). The standard deviation was divided by the square root of the number of replicates of the sample to give the standard error.

The results obtained are shown in FIG. 1 of the drawings. The dark bars show how the native cells react with the anti-D 'K', but not with any of the other binding agent probes. Once sensitised with anti-D 'K' (pale bars), the cells do not react with the anti-D 'K' probe, but give very high S/N against the anti-IgG probes. The anti-C3 gives no cross-reactivity. Thus it may be seen that DAT testing can be successfully achieved using a protein microarray platform.

EXAMPLE 6

DAT Testing of Blood Using Protein Microarrays

A chamber was placed over each of the protein microarrays prepared according to Example 3. A blood sample from a subject was washed at least 4 times in PBS. An RBC solution for adding to the microarray was prepared by suspending the blood sample to a 1% haematocrit in PBS-BSA. 450 l of the RBC solution was then pipetted through one of the portholes in the chamber onto the microarray slides. The portholes were sealed with the provided port seals. The slides were placed in a slide box and mixed for one hour at room temperature.

In this example the RBC blood samples contained group O $R_1r$ cells sensitized with anti-D 'K' (LHM169/80).

The chamber was removed and slides briefly submerged into PBS to remove excess target solution. This was followed by two washes in PBS for 10 minutes. After the final wash the slides were centrifuged to dryness and stored in a dust-free dark place until scanning. Data was extracted as in Example 5.

Figure 2:
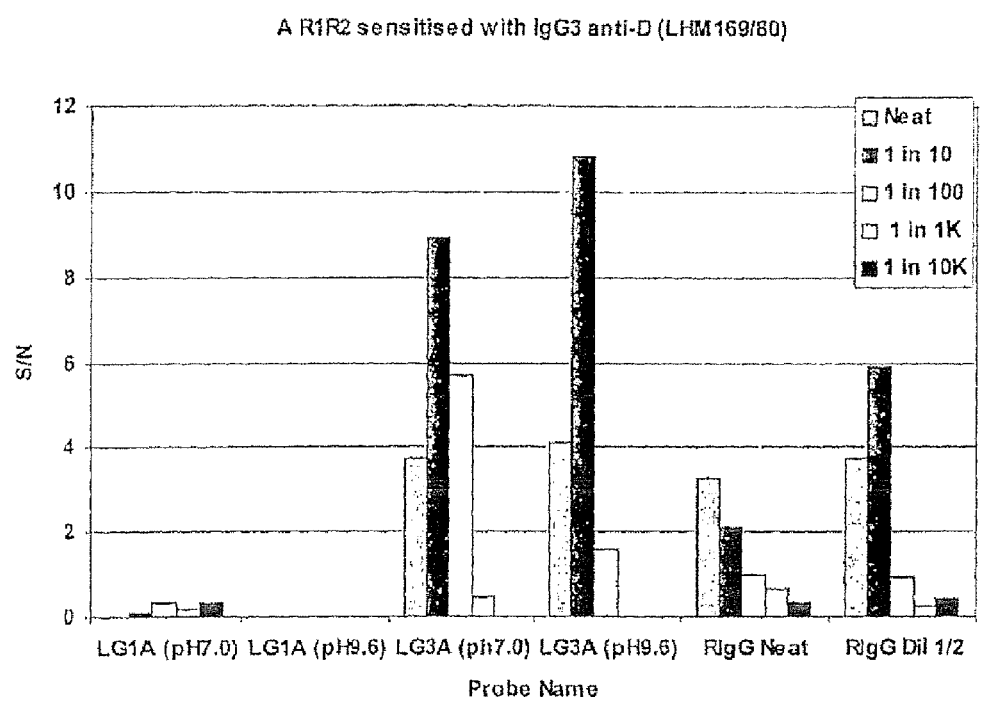
FIG. 2 depicts the results of the DAT testing of blood using protein microarrays as described in Example 6.

The results obtained are shown in FIG. 2 of the drawings. The different coloured bars demonstrate the dilution factor of the sensitizing antibody. The antibody used in this example is LHM169/80, which is an $IgG_3$. The results demonstrate specific binding to both anti-$IgG_3$ (LG3A) and to the rabbit anti-IgG. The probes are also spotted at two different pH, demonstrating that alteration of pH spotting buffer can adjust reactivity during incubation with test samples. The dilution of the sensitizing antibody is evident in the data. However, when sensitizing with neat anti-D the S/N is reduced, most likely due to sample overload causing material to leave the spot. The highest S/N is demonstrated with sensitizing antibody at 1 in 10 dilution.

EXAMPLE 7

DAT Testing of Blood Using Protein Microarrays

All protocols were as described previously. In this example the RBC blood samples contained group O $R_1r$ cells sensitized with anti-D 'H' (LHM77/64).

Figure 3:
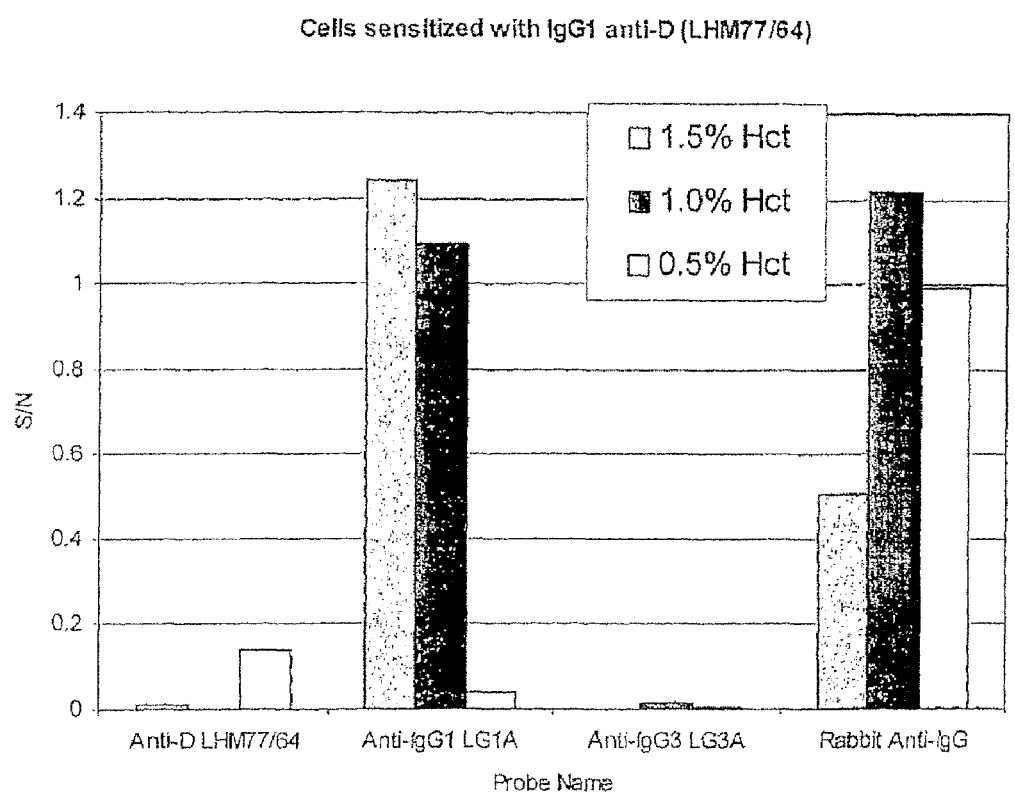
FIG. 3 depicts the results of the DAT testing of blood using protein microarrays as described in Example 7.

The results obtained are shown in FIG. 3 of the drawings. The different coloured bars demonstrate the dilution factor of the sensitizing antibody. The antibody used in this example is LHM77/64, which is an $IgG_1$. The results demonstrate specific binding to both anti-$IgG_1$ (LG1A) and to the rabbit anti-IgG, with almost no binding to the anti-$IgG_3$. In this experiment, different cell suspensions were used to determine if altering haematocrit alters specific binding. Overall the 1% suspension demonstrates most consistency. In this example, binding of the sensitized cells is blocked to the anti-D LHM77/64.

REFERENCES

Robb. J. S., Roy, D. J., Ghazal, P., Allan, J. and Petrik, J. (2006). "Development of non-agglutination microarray blood grouping" Transfusion Medicine. 16, 119-129.

Campbell, C. J., O'Looney, N., Chong Kwan, M., Robb, J. S., Ross, A. J., Beattie, J. S., Petrik, J. and Ghazal, P. (2006). "Cell Interaction Microarray for Blood Phenotyping" Analytical Chemistry. 78, 1930-1938.

The invention claimed is:

1. A blood testing method to confirm the detection of a disease in a subject, wherein the disease is characterised by the presence of at least one characteristic antibody/complement factor bound to the surface of the red blood cells of the subject, comprising the steps of:
   providing a microarray wherein a plurality of binding agents which are capable of binding specifically to different characteristic antibodies or compliment factors on the red blood cells are immobilised on a substrate at discrete predefined positions;
   contacting a blood sample from the subject with said microarray;
   substantially removing any unbound red blood cells from at least an area of said substrate on which said binding agents are immobilised; and
   detecting the presence or red blood cells bound to the microarray through said characteristic antibodies or complement factors, wherein the presence of any red blood cells bound to the microarray indicates the presence of said characteristic antibody/complement factor bound to the red blood cells of the subject so as to confirm detection of said disease.

2. A method according to claim 1 wherein the binding agent is a monoclonal antibody.

3. A method according to claim 1 wherein the binding agent is polyclonal antibody.

4. A method according to claim 1 wherein the binding agent is a chimeric antibody.

5. A method according to claim 1 wherein the binding agent is a single chain antibody.

6. A method according to claim 1 wherein the binding agent is selected from monoclonal anti-$IgG_1$, monoclonal anti-$IgG_3$ and monoclonal anti-C3.

7. A method according to claim 3 wherein polyclonal anti-IgG binding agent is included.

8. A method according to claim 1 wherein at least two different binding agents are immobilised in discrete areas of the substrate.

9. A method according to claim 8 wherein each binding agent is provided in a number of different dilutions.

10. A method according to claim 9 wherein each binding agent is repeated a number of times at a given dilution.

11. A method according to claim 1 wherein the substrate is made of glass, gold silicon, silicon oxide, metals and metal oxides; either bare or functionalised with functional polymer.

12. A method according to claim 11 wherein the substrate is a gold-coated substrate.

13. A method according to claim 12 wherein the gold is functionalised such that the binding agents are capable of being immobilised thereon.

14. A method according to claim 13 wherein the functionalisation is such that the distance between the gold surface and a bound red blood cell can be controlled.

15. A method according to claim 1 wherein the microarray is formed on a planar or spheroid surface.

16. A method according to claim 1 wherein the substrate is a rigid or semi-rigid support selected from the group consisting of membranes, filter chips, slides, wafers, fibers, magnetic or non-magnetic beads, gels, tubing, plates, polymers, microparticles and capillaries.

17. A method according to claim 1 wherein the binding agent is immobilised in spots less than 1 mm in diameter.

18. A method according to claim 1 wherein the substrate comprises a plurality of separate arrays on the surface of the substrate, arranged in a manner to allow separate samples to be contacted with each array in such a way that the samples do not mix.

19. A method according to claim 1 wherein areas of the substrate not provided with binding agent are treated with blocking agents in order to minimise any non-specific binding.

20. A method according to claim 1 wherein bound red blood cells are detected by secondary labelling detection.

* * * * *

UNITED STATES PATENT AND TRADEMARK OFFICE
CERTIFICATE OF CORRECTION

| | | |
|---|---|---|
| PATENT NO. | : 8,030,006 B2 | Page 1 of 1 |
| APPLICATION NO. | : 12/441784 | |
| DATED | : October 4, 2011 | |
| INVENTOR(S) | : Robb et al. | |

It is certified that error appears in the above-identified patent and that said Letters Patent is hereby corrected as shown below:

In the Claims:

Column 10, Claim 1, Line 38:   Please correct "the red blood cells"
                                                to read -- said red blood cells --

Signed and Sealed this
Third Day of January, 2012

David J. Kappos
*Director of the United States Patent and Trademark Office*